(12) United States Patent
Walters et al.

(10) Patent No.: US 11,338,265 B2
(45) Date of Patent: May 24, 2022

(54) METHOD FOR PREPARING MICROCAPSULES AND MICROPARTICLES OF CONTROLLED SIZE

(71) Applicant: CALYXIA, Bonneuil-sur-Marne (FR)

(72) Inventors: Jamie Walters, Paris (FR); Damien Demoulin, Paris (FR)

(73) Assignee: CALYXIA, Bonneuil-sur-Marne (FR)

( * ) Notice: Subject to any disclaimer, the term of this patent is extended or adjusted under 35 U.S.C. 154(b) by 204 days.

(21) Appl. No.: 16/465,970

(22) PCT Filed: Dec. 1, 2017

(86) PCT No.: PCT/EP2017/081273
§ 371 (c)(1),
(2) Date: May 31, 2019

(87) PCT Pub. No.: WO2018/100196
PCT Pub. Date: Jun. 7, 2018

(65) Prior Publication Data
US 2019/0299185 A1   Oct. 3, 2019

(30) Foreign Application Priority Data

Dec. 1, 2016 (FR) ..................... 16 61794

(51) Int. Cl.
| | |
|---|---|
| *B01J 13/14* | (2006.01) |
| *A61K 8/895* | (2006.01) |
| *A23L 27/00* | (2016.01) |
| *A61K 9/50* | (2006.01) |
| *A61Q 19/00* | (2006.01) |
| *C09B 67/30* | (2006.01) |
| *A01N 25/28* | (2006.01) |
| *A61K 8/11* | (2006.01) |
| *C08F 2/22* | (2006.01) |
| *C09B 67/46* | (2006.01) |
| *B01F 3/08* | (2006.01) |

(52) U.S. Cl.
CPC ............. *B01J 13/14* (2013.01); *A01N 25/28* (2013.01); *A23L 27/72* (2016.08); *A61K 8/11* (2013.01); *A61K 8/895* (2013.01); *A61K 9/50* (2013.01); *A61Q 19/00* (2013.01); *C08F 2/22* (2013.01); *C09B 67/009* (2013.01); *C09B 67/0078* (2013.01); *A61K 9/5026* (2013.01); *A61K 9/5031* (2013.01); *A61K 9/5089* (2013.01); *A61K 2800/10* (2013.01); *B01F 3/0811* (2013.01); *B01F 2003/0846* (2013.01)

(58) Field of Classification Search
CPC ... B01J 13/18; B01J 13/14; C08F 2/30; C08F 2/50; C08F 2/22; C09K 5/063; F28D 20/023; A01N 25/02; A23L 27/72; A61K 8/11; A61K 8/895; A61K 9/50; A61K 9/5026; A61K 9/5031; A61K 9/5089; A61K 2800/10; A61Q 19/00; C09B 67/0078; C09B 67/009; B01F 3/0811; B01F 2003/0846
See application file for complete search history.

(56) References Cited

U.S. PATENT DOCUMENTS

| | | | |
|---|---|---|---|
| 6,951,836 B2 | 10/2005 | Jahns et al. | |
| 2010/0180995 A1* | 7/2010 | Teratani | B60C 17/066 |
| | | | 152/157 |
| 2012/0076843 A1 | 3/2012 | Jung | |

FOREIGN PATENT DOCUMENTS

| | | | | |
|---|---|---|---|---|
| EP | 1 502 646 A1 | 2/2005 | | |
| EP | 3 144 058 A1 | 3/2017 | | |
| EP | 3 144 059 A1 | 3/2017 | | |
| WO | WO-2017046360 A1 * | 3/2017 | | A61K 8/87 |

OTHER PUBLICATIONS

International Search Report & Written Opinion, dated Apr. 13, 2018, in International Patent Application No. PCT/EP2017/081273.

\* cited by examiner

*Primary Examiner* — Irina S Zemel
(74) *Attorney, Agent, or Firm* — Knobbe Martens Olson & Bear, LLP

(57) ABSTRACT

The present invention relates to a method for the preparation of microparticles and solid microcapsules comprising the following steps:
  a) the addition, with stirring, of composition C'2 in a composition C3, the compositions C'2 and C3 not being miscible with each other, the composition C'2 being either a monophasic composition C2 or an emulsion (E1) comprising drops of a composition C1, comprising at least one active ingredient, dispersed in a polymeric composition C2, the compositions C1 and C2 not being miscible in each other, the viscosity of composition C3 being greater than 10,000 mPa·s at 25° C. at a shear rate of $s^{-1}$ and being less than 10,000 mPa·s at 25° C. at a shear rate of between 100 $s^{-1}$ and 100,000 $s^{-1}$, wherein an emulsion (E2) is obtained
  b) applying shear to the emulsion (E2), the applied shear rate being less than 1000 $s^{-1}$, wherein an emulsion (E3) is obtained; and
  c) the polymerization of the composition C'2.

16 Claims, 3 Drawing Sheets

METHOD FOR PREPARING MICROCAPSULES AND MICROPARTICLES OF CONTROLLED SIZE

PRIORITY AND CROSS REFERENCE TO RELATED APPLICATIONS

This application is the U.S. National Phase Application under 35 U.S.C. § 371 of International Application No. PCT/EP2017/081273, filed Dec. 1, 2017, designating the U.S. and published as WO 2018/100196 A1 on Jun. 7, 2018, which claims the benefit of French Application No. FR 16 61794, filed Dec. 1, 2016. Any and all applications for which a foreign or a domestic priority is claimed is/are identified in the Application Data Sheet filed herewith and is/are hereby incorporated by reference in their entireties under 37 C.F.R. § 1.57.

FIELD

The present disclosure relates to a method for preparing microcapsules and microparticles.

SUMMARY

The present disclosure relates to a method for the preparation of controlled-size microparticles and microcapsules in the absence of photopolymerization.

DETAILED DESCRIPTION

Figure 1:
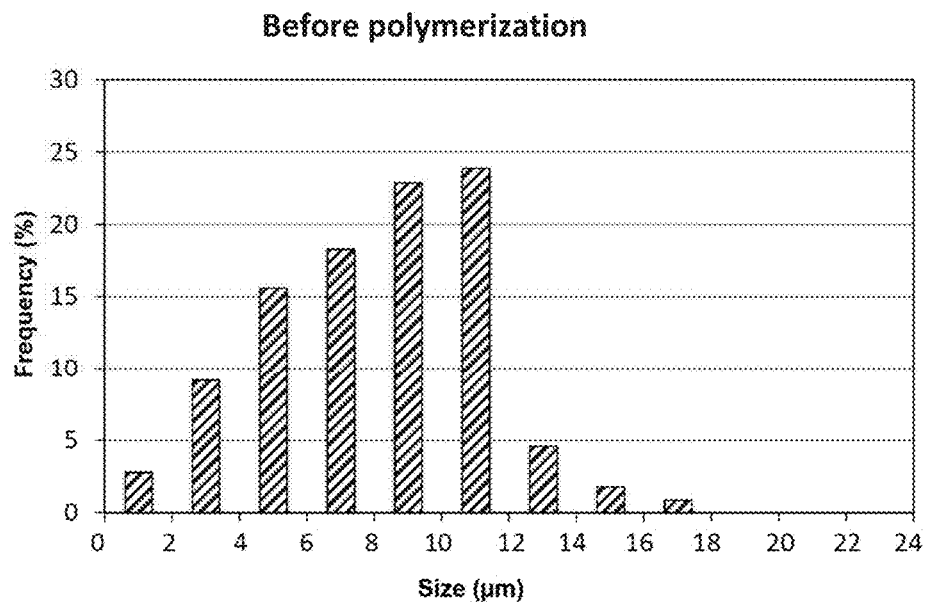
FIG. 1 shows the size distributions of the capsules obtained at different stages of an embodiment of the method of the present disclosure.

The present invention relates to a method for the preparation of controlled-size microparticles and microcapsules in the absence of photopolymerization.

In many industries, including the chemical, cosmetic, agrochemical, paint or fuel and lubricant industries, it is important to encapsulate and isolate an active ingredient from the surrounding environment, in order to protect the active against hydrolysis, thermal degradation, oxidation or other processes that may reduce the performance of the active ingredient. In addition, many applications within these industries require that the particles or capsules produced have a narrow size range typically in the micrometer range (especially between 0.1 µm and 20 µm) for example, in order to have better control over their overall performance.

In many products made by the chemical industry such as cosmetics, paints, coatings or mastics, polymer microparticles are sometimes added to modify their rheological properties or texture. The rheological performance achieved is extremely dependent on the average size of the microparticles as well as the size range in which they extend (commonly called the size distribution).

The issue of isolating an active ingredient from the surrounding environment to improve active ingredient performance is a relatively new area for a number of industries. In most non-organic industries, performance losses associated with factors such as hydrolysis, thermal degradation, oxidation, and cross-reactivity are resolved by increasing the concentration of the active ingredient to achieve the desired level of performance, but which increases the cost and also generates other problems associated with the product formed with such methods.

In recent years, a large number of particle or capsule manufacturing methods have been developed and reported in the literature, including spray drying, solvent evaporation, interfacial polymerization and centrifugal extrusion among many others. However, for manufacturing methods of particles and capsules on an industrial scale, emulsion techniques dominate. Such methods use a step forming an emulsion of a hydrophobic oil or a waxy phase dispersed in an aqueous medium, or, alternatively, an aqueous phase dispersed in a hydrophobic oil or a waxy medium. The two phases are emulsified using either a homogenizer or a stirred vessel equipped with baffles, and stabilized using surfactants, lipids or polymeric emulsifiers. Alternatively, a reaction at the interface between the two phases may be used for the formation of a polymer envelope.

However, these systems produce emulsions and capsules that are polydisperse or are too large (above 20 µm).

In addition, these systems require the use of water to form one of the phases. They also require the use of surfactants or similar emulsifiers to stabilize the emulsion, but which have the disadvantage of being able to react with the encapsulant or providing contaminants in the different phases.

The present invention aims to provide particles and capsules containing an active ingredient by implementing a bulk method to meet the volumes to meet the demands of non-biologic industries.

The present invention also aims to provide an emulsification method for obtaining particles and capsules of controlled-size, in particular less than 20 µm, or even 5 µm.

The present invention also aims to provide an encapsulation method of actives that may be implemented in the absence of water and/or surfactants and emulsifiers.

The present invention also aims to provide manufacturing method of microparticles and microcapsules using emulsions consisting of materials that make the drops that compose them, on the one hand, monodisperse and, on the other hand, extremely stable.

Thus, the present invention relates to a method for preparing microparticles and solid microcapsules comprising the following steps:
a) the addition, with stirring, of a composition C'2 in a composition C3, the compositions C'2 and C3 not being miscible with each other,
the composition C'2 being either a cross-linkable monophasic composition C2 or an emulsion (E1) comprising drops of a composition C1, comprising at least one active ingredient, dispersed in a crosslinkable polymeric composition C2, the compositions C1 and C2 not being miscible with each other,
the viscosity of composition C3 being greater than 10,000 mP·s at 25° C. at a shear rate of 10 s$^{-1}$ and being less than 10,000 mP·s at 25° C. at a shear rate of between 100 s$^{-1}$ and 100,000 s$^{-1}$,
wherein an emulsion (E2) comprising drops of composition C'2 dispersed in composition C3 is obtained;

b) applying a shear to the emulsion (E2), the applied shear rate being between 100 s$^{-1}$ and 100,000 s$^{-1}$,
wherein an emulsion (E3) is obtained comprising controlled-size drops of composition C'2 dispersed in the composition C3; and
c) the polymerization of the composition C'2, wherein microparticles or solid microcapsules dispersed in the composition C3 are obtained.

Depending on the nature of the composition C'2, the method of the invention makes it possible to obtain microparticles or microcapsules. When the composition C'2 comprises at least one active ingredient, we then speak of microcapsules.

Depending on the nature of the composition C'2, the emulsion (E2) is either a simple emulsion comprising drops of composition C2 dispersed in the composition C3, or a double emulsion comprising drops dispersed in the composition C3 (corresponding to the emulsion (E'2) mentioned below).

Depending on the nature of the composition C'2, the emulsion (E3) is either a simple emulsion comprising controlled-size drops of composition C2 dispersed in the composition C3, or a double emulsion comprising controlled-size drops dispersed in the composition C3 (corresponding to the emulsion (E'2) mentioned below).

According to one embodiment, the method of the invention comprises the following steps:
a") the addition, with stirring, of a crosslinkable composition C2 in a composition C3, the compositions C2 and C3 not being miscible with each other,
the viscosity of composition C3 being greater than 10,000 mP·s at 25° C. at a shear rate of 10 s$^{-1}$ and being less than 10,000 mP·s at 25° C. at a shear rate of between 100 s$^{-1}$ and 100,000 s$^{-1}$,
wherein an emulsion (E2) is obtained comprising drops of composition C2 dispersed in composition C3;
b) applying a shear to the emulsion (E2), the applied shear rate being between 100 s$^{-1}$ and 100,000 s$^{-1}$, wherein an emulsion (E3) is obtained comprising controlled-size drops of composition C2 dispersed in the composition C3; and
c) the polymerization of the composition C2, wherein solid microparticles dispersed in the composition C3 are obtained.

According to this embodiment, the method of the invention thus allows the production on an industrial scale of populations of emulsion drops with a controlled size and in particular less than 20 µm. The control of the size of the drops obtained by the method of the invention is due, in particular, to the control of the rheological properties of the continuous phase C3.

According to this embodiment, the method of the invention allows the production of microparticles of controlled-size by the implementation of a step of polymerization of the emulsion drops. This polymerization step, in particular, makes it possible to solidify the drops and thus eliminates any coalescence.

According to another embodiment, the aforementioned composition C'2 is an emulsion (E1) obtained by the addition, with stirring, of a composition C1 comprising at least one active ingredient, in a crosslinkable polymeric composition C2, the compositions C1 and C2 not being miscible with each other.

According to this embodiment, the method of the invention comprises the following steps:
a1) the addition, with stirring, of a composition C1, comprising at least one active ingredient, in a crosslinkable composition C2, the compositions C1 and C2 not being miscible with each other, wherein an emulsion (E1) comprising drops of composition C1 dispersed in composition C2, is obtained;
a2) the stirring addition of the emulsion (E1) in a composition C3, the compositions C2 and C3 not being miscible with each other, the viscosity of composition C3 being greater than 10,000 mP·s at 25° C. at a shear rate of 10 s$^{-1}$ and being less than 10,000 mP·s at 25° C. at a shear rate of between 100 s$^{-1}$ and 100,000 s$^{-1}$, wherein a double emulsion (E'2) is obtained comprising drops dispersed in the composition C3;
b) applying shear to the emulsion (E'2), the applied shear rate being between 100 s$^{-1}$ and 100,000 s$^{-1}$, wherein a double emulsion (E'3) is obtained comprising controlled-size drops dispersed in the composition C3; and
c) the polymerization of the composition C2, wherein solid microcapsules dispersed in the composition C3 are obtained.

According to this embodiment, the method of the invention thus allows the production on an industrial scale of populations of controlled-size drops of a double emulsion and, in particular, less than 20 µm. The control of the size of the drops obtained by the method of the invention is due, in particular, to the control of the rheological properties of the continuous phase C3.

According to this embodiment, the method of the invention allows the production of controlled-size capsules by the implementation of a polymerization step of the intermediate phase of the double emulsion. This polymerization step makes it possible, in particular, to solidify the intermediate layer of the capsules and thus eliminates any coalescence.

Preferably, the microparticles and the microcapsules obtained according to the method of the invention have a mean diameter (as measured by optical microscopy or by TEM or by light scattering technique) of between 0.1 µm and 20 µm, and preferably between 1 µm and 20 µm.

Step a)

During step a), a composition C'2 is added to a composition C3, this step being carried out with stirring, which means that the composition C3 is agitated, typically mechanically, while the composition C'2 is added in order to emulsify the mixture of compositions C'2 and C3.

The addition of the composition C'2 in the composition C3 is typically carried out dropwise.

According to one embodiment, the composition C'2 may be an emulsion (E1) as defined above. This emulsion (E1) is prepared according to step a1) as described below.

During step a1), a composition C1 is added to a crosslinkable composition C2, this step being carried out with stirring, which means that the composition C2 is stirred, typically mechanically, while the composition C1 is added, in order to emulsify the mixture of compositions C1 and C2.

The addition of the composition C1 in the composition C2 is typically carried out dropwise.

During step a1), the composition C1 is at a temperature between 0° C. and 100° C., preferably between 10° C. and 80° C., and preferably between 15° C. and 60° C. During step a1), the composition C2 is at a temperature between 0° C. and 100° C., preferably between 10° C. and 80° C., and preferably between 15° C. and 60° C.

Under the conditions of addition of step a1), the compositions C1 and C2 are not miscible with each other, which means that the amount (by weight) of the composition C1 capable of being solubilized in the composition C2 is less than or equal to 5%, preferably less than 1%, and preferably less than 0.5%, relative to the total weight of composition C2, and that the amount (by weight) of the composition C2 capable of being solubilized in composition C1 is less than or equal to 5%, preferably less than 1%, and preferably less than 0.5%, relative to the total weight of composition C1.

Thus, when the composition C1 comes into contact with the composition C2 with stirring, the latter is dispersed in the form of drops, called single drops.

The immiscibility between compositions C1 and C2 also makes it possible to avoid the migration of the active ingredient from composition C1 to composition C2.

Composition C2 is stirred to form an emulsion comprising drops of composition C1 dispersed in composition C2. This emulsion is also called "simple emulsion" or C1-in-C2 emulsion.

To implement step a1), it is possible to use any type of stirrer usually used to form emulsions, such as, for example, a mechanical stirrer, a static emulsifier, an ultrasonic homogenizer, a membrane homogenizer or a high pressure homogenizer, a colloid mill, a high shear disperser or a high speed homogenizer, may be used.

Composition C1

The composition C1 comprises at least one active ingredient A. In the method of the invention, this composition C1 serves as a carrier for the active ingredient A within the drops formed during the method of the invention and the solid capsules so obtained.

According to a first variant of the method of the invention, the composition C1 is monophasic, i.e. it is the pure active ingredient A or a solution comprising the active ingredient A in solubilized form.

According to one embodiment, the active ingredient is solubilized in composition C1.

According to this variant, the composition C1 typically consists of a solution of the active ingredient A in an aqueous solution, or an organic solvent, or a mixture of organic solvents, the active ingredient A being present in a weight content of between 1% and 99%, relative to the total weight of the composition C1. The active ingredient A may be present in a weight content ranging from 5% to 95%, from 10% to 90%, from 20% to 80%, from 30% to 70%, or from 40% to 60%, relative to the total weight of the composition C1.

According to one embodiment, the composition C1 consists of the active ingredient A.

According to another embodiment of the invention, the composition C1 is a biphasic composition, which means that the active ingredient is dispersed, either in liquid form or in solid form, in the composition C1, and is not totally solubilized in the composition C1.

According to one embodiment, the active ingredient is dispersed in the form of solid particles in the composition C1.

According to this embodiment, the composition C1 may consist of a dispersion of solid particles of the active ingredient in an organic solvent or in a mixture of organic solvents.

According to this embodiment, the composition C1 may consist of a dispersion of solid particles of the active ingredient in an aqueous phase, which comprises water and optionally hydrophilic organic solvents.

The active ingredient used is for example:
- a crosslinking agent, a hardener, an organic or metal catalyst (such as an organometallic or inorganometallic complex of platinum, palladium, titanium, molybdenum, copper, zinc) used to polymerize polymer and elastomer formulations; rubber, paint, adhesive, seal, mortar, varnish or coating;
- a dye or a pigment for formulations of elastomers, paint, coating, adhesive, seal, mortar, or paper;
- a fragrance (as defined by the International Fragrance Association (IFRA) molecule list and available on the www.ifraorg.org website) for detergents such as detergent products, home care products, cosmetic and personal care products, textiles, paints, coatings;
- an aroma, a vitamin, an amino acid, a protein, a lipid, a probiotic, an antioxidant, a pH corrector, a preservative for the food compounds and animal feed;
- a softener, a conditioner for detergents, detergent products, cosmetics and personal care products. As such, the usable active ingredients are for example listed in U.S. Pat. Nos. 6,335,315 and 5,877,145;
- an anti-discoloration agent (such as an ammonium derivative), an antifoam agent (such as an alcohol ethoxylate, an alkylbenzene sulfonate, a polyethylene ethoxylate, an alkylethoxysulphate or alkylsulphate) for detergents and detergent products and home care products;
- a brightening agent, also called a color activator (such as a stilbene derivative, a coumarin derivative, a pyrazoline derivative, a benzoxazole derivative or a naphthalimide derivative) intended for detergents, detergent products, cosmetics and personal care products;
- a biologically-active compound such as an enzyme, a vitamin, a protein, a plant extract, an emollient agent, a disinfecting agent, an antibacterial agent, an anti-UV agent, a drug intended for cosmetic and skincare products to textiles. These biologically-active compounds include: vitamins A, B, C, D and E, para-aminobenzoic acid, alpha hydroxy acids (such as glycolic acid, lactic acid, malic acid, tartaric acid or citric acid), camphor, ceramides, polyphenols (such as flavonoids, phenolic acid, ellagic acid, tocopherol, ubiquinol), hydroquinone, hyaluronic acid, isopropyl isostearate, isopropyl palmitate, oxybenzone, panthenol, proline, retinol, retinyl palmitate, salicylic acid, sorbic acid, sorbitol, triclosan, tyrosine;
- a disinfecting agent, an antibacterial agent, an anti-UV agent, for paints and coatings;
- a fertilizer, herbicide, insecticide, pesticide, fungicide, repellent or disinfectant for agrochemicals;
- a flame retardant (such as a brominated polyol such as tetrabromobisphenol A, a halogenated or non-halogenated organophosphorus compound, a chlorinated compound, an aluminum trihydrate, an antimony oxide, a zinc borate, red phosphorus, melamine, or magnesium dihydroxide) for use in plastics, coatings, paints and textiles;
- a photonic crystal or photochromophore for paints, coatings and polymeric materials forming curved and flexible screens;
- a product known to those skilled in the art as phase change materials (PCM) capable of absorbing or returning heat when they undergo a phase change, intended for the storage of 'energy. Examples of PCM and their applications are described in Farid et al., Energy Conversion and Management, 2004, 45 (9-10), 1597-1615. of PCM, mention may be made of molten salts of aluminum phosphate, ammonium carbonate, ammonium chloride, cesium carbonate, cesium sulfate, calcium citrate, calcium chloride, calcium hydroxide, calcium oxide, calcium phosphate, calcium saccharate, calcium sulfate, cerium phosphate, iron phosphate, lithium carbonate, lithium sulfate, magnesium chloride, magnesium sulphate, manganese chloride, manganese nitrate, manganese sulphate, potassium acetate, potassium carbonate, potassium chloride, potassium phosphate, rubidium carbonate, rubidium sulphate, disodium tetraborate, sodium acetate, sodium bicarbonate, sodium bisulfate, sodium citrate, sodium chloride, sodium hydroxide, sodium nitrate, sodium percarbonate, sodium persulfate, sodium phosphate, sodium propionate, sodium selenite, sodium silicate, sodium sulfate, sodium tellurate, sodium thiosulfate, strontium hydrophosphate, zinc acetate, zinc chloride, sodium thiosulfate, waxes paraffinic hydrocarbons, polyethylene glycols.

According to one embodiment, the composition C'2 may be a composition C2 as defined above.

According to this embodiment, step a) corresponds to step a") described above.

During step a"), a crosslinkable composition C2 is added to a composition C3, this step being carried out with stirring, which means that the composition C3 is stirred, typically mechanically, while the composition C2 is added in order to emulsify the mixture of compositions C2 and C3.

The addition of the composition C2 to the composition C3 is typically carried out dropwise.

During step a"), the composition C2 is at a temperature between 0° C. and 100° C., preferably between 10° C. and 80° C., and preferably between 15° C. and 60° C. During step a"), the composition C3 is at a temperature between 0° C. and 100° C., preferably between 10° C. and 80° C., and preferably between 15° C. and 60° C.

Under the conditions of addition of step a"), the compositions C2 and C3 are not miscible with each other, which means that the amount (by weight) of the composition C2 capable of being solubilized in the composition C3 is less than or equal to 5%, preferably less than 1%, and preferably less than 0.5%, relative to the total weight of composition C3, and that the amount (by weight) of the composition C3 capable of being solubilized in composition C2 is less than or equal to 5%, preferably less than 1%, and preferably less than 0.5%, relative to the total weight of composition C2.

Thus, when the composition C2 comes into contact with the composition C3 with stirring, the latter is dispersed in the form of drops, called single drops.

The immiscibility between compositions C2 and C3 also makes it possible to avoid the migration of the active ingredient from composition C2 to composition C3.

The composition C3 is stirred to form an emulsion comprising drops of composition C2 dispersed in the composition C3. This emulsion is also called "simple emulsion" or C2-in-C3 emulsion.

To carry out step a"), it is possible to use any type of stirrer usually used to form emulsions, such as for example an ultrasonic homogenizer, a membrane homogenizer, a high-pressure homogenizer, a colloid mill, a high shear disperser or a high speed homogenizer.

Composition C2

The composition C2 is a crosslinkable composition which means that it is a composition capable of polymerizing (crosslinking) to give a solid material in order to form the polymerized envelope of the solid microcapsules of the invention.

According to the invention, the composition C2 is not a photocrosslinkable composition.

According to one embodiment, the composition C2 is a liquid whose viscosity at 25° C. is between 500 mP·s and 100,000 mP·s at a shear rate of 10 s$^{-1}$.

The viscosity is measured by means of a Haake Rheostress™ 600 rheometer equipped with a cone of diameter 60 mm and angle 2 degrees, and a temperature control cell set at 25° C.

Preferably, the viscosity of composition C2 at 25° C. is between 1000 mP·s and 50,000 mP·s at a shear rate of 10 s$^{-1}$, preferably between 2000 mP·s and 25000 mP·s, and, for example, between 3,000 mP·s and 15,000 mP·s.

Preferably, the viscosity of the composition C2 is greater than the viscosity of the composition C1.

According to this embodiment, regardless of the viscosity of the active ingredient or its chemical properties, the destabilization kinetics of the drops of the emulsion (E1) is significantly slow, which allows the envelope of the microcapsules to be polymerized during step d) before the emulsion is destabilized. Once completed, the polymerization then provides a thermodynamic stabilization.

Thus, the relatively high viscosity of the composition C2 ensures the stability of the emulsion (E1) obtained at the end of step a).

Preferably, the interfacial tension between compositions C1 and C2 is low. Typically, these interfacial tensions vary between 0 mN/m and 50 mN/m, preferably between 0 mN/m and 20 mN/m.

The low interfacial tension between the compositions C1 and C2 also advantageously makes it possible to ensure the stability of the emulsion (E1) obtained at the end of step a1).

According to one embodiment, the ratio between the volume of composition C1 and the volume of composition C2 varies between 1:10 and 10:1. Preferably, this ratio is between 1:3 and 5:1, preferably between 1:3 and 3:1.

This ratio may be adapted to control the thickness of the envelope of the polymerized microcapsules.

According to one embodiment, the composition C2 comprises at least one monomer or polymer, at least one crosslinking agent, and optionally at least one catalyst.

According to an advantageous embodiment, the composition C2 does not comprise a photoinitator.

According to one embodiment, the composition C2 comprises from 50% to 99% by weight of monomer or polymer, or a mixture of monomers or polymers, relative to the total weight of the composition C2.

According to one embodiment, the composition C2 comprises from 1% to 20% by weight of crosslinking agent or of a mixture of crosslinking agents, relative to the total weight of the composition C2.

According to one embodiment, the composition C2 comprises from 0.001% to 5% by weight of catalyst or a mixture of catalysts, relative to the total weight of the composition C2.

According to one embodiment, the composition C2 comprises from 0.001% to 70% by weight of crosslinking agent relative to the total weight of composition C2.

According to the invention, the term "monomer" or "polymer" denotes any base unit suitable for the formation of a solid material by polymerization, either alone or in combination with other monomers or oligomers.

These monomers may be chosen from monomers comprising at least one reactive functional group chosen from the group consisting of acrylate, methacrylate, vinyl ether, N-vinyl ether, mercaptoester, thiolene, siloxane, epoxy, oxetane, urethane, isocyanate and peroxide functions.

In particular, the monomers may be chosen from monomers bearing at least one of the aforementioned reactive functional groups and additionally bearing at least one functional group selected from the group consisting of primary, secondary and tertiary alkylamine functions, quaternary amine functional groups, and functions of sulfate, sulfonate, phoshate, phosphonate, carboxylate, hydroxyl, halogen, and mixtures thereof.

The polymers used in the composition C2 may be chosen from polyethers, polyesters, polyurethanes, polyureas, polyethylene glycols, polypropylene glycols, polyamides, polyacetals, polyimides, polyolefins, polysulphides and polydimethylsiloxanes, the polymers additionally bearing at least one reactive function chosen from the group consisting of acrylate, methacrylate, vinyl ether, N-vinyl ether, mercaptoester, thiolene, siloxane, epoxy, oxetane, urethane, isocyanate and peroxide functions.

Examples of such monomers or oligomers include, but are not limited to, the following polymers: poly(2-(1-naphthyloxy)-ethyl acrylate), poly(2-(2-naphthyloxy)-ethyl acrylate) poly(2-(2-naphthyloxy)-ethyl methacrylate), polysorbitol dimethacrylate, polyacrylamide, poly((2-(1-naphthyloxy) ethanol), poly(2-(2-naphthyloxy) ethanol), poly(1-chloro) 2,3-epoxypropane), poly(n-butyl isocyanate), poly(N-vinyl carbazole), poly(N-vinyl pyrrolidone), poly(p-benzamide), poly(p-chlorostyrene), poly(p-methyl styrene), poly(p-phenylene oxide), poly(p-phenylene sulfide), poly(N-(methacryloxyethyl) succinimide), polybenzimidazole, polybutadiene, polybutylene terephthalate, polychloral, polychloro trifluoroethylene, polyether imide, polyether ketone, polyether sulfone, polyhydridosilsesquioxane, poly(m-phenylene isophthalamide), poly(methyl 2-acrylamido-2-methoxyacetate), poly(2-acrylamido-2-methylpropanesulfonic acid), poly-mono-butyl maleate, polybutylmethacrylate, poly(N-tert-butylmethacrylamide), poly(Nn-butylmethacrylamide), polycyclohexylmethacrylamide, poly(m-xylenebisacrylamide 2,3-dimethyl-1,3-butadiene,N,N-dimethylmethacrylamide), poly(n-butyl methacrylate), poly(cyclohexyl methacrylate), polyisobutyl methacrylate, poly(4-cyclohexylstyrene), polycyclol acrylate, polycyclol methacrylate, polydiethyl ethoxymethylenemalonate, poly(2,2,2-trifluoroethyl methacrylate), poly(1, 1,1-trimethylolpropane) trimethacrylate), polymethacrylate, poly(N,N-dimethylaniline, dihydrazide), polyfisophthalic dihydrazine), isophthalic polyacid, polydimethyl benzilketal, epichlorohydrin, poly(ethyl-3,3-diethoxyacrylate), poly(ethyl-3,3-dimethylacrylate) poly(ethyl vinyl ketone), poly(vinyl ethyl ketone), poly(penten-3-one), polyformaldehyde poly(diallyl acetal), polyfumaronitrile, polyglyceryl propoxy triacrylate, polyglyceryl trimethacrylate, polyglycidoxypropyltrimethoxysilane, polyglycidyl acrylate, poly (n-heptyl acrylate), poly(n-heptyl ester of acrylic acid), poly(n-heptyl methacrylate), poly(3-hydroxypropionitrile), poly(2-hydroxypropyl acrylate), poly(2-hydroxypropyl methacrylate), poly(N-(methacryloxyethyl) phthalimide), poly(1,9-nonanediol diacrylate), poly(1,9-nonanediol dimethacrylate), poly(N-(n-propyl) acrylamide), poly(orthoacrylic acid)-phthalic), poly(iso-phthalic acid), poly(1,4-benzenedicarboxylic acid), poly(1,3-benzenedicarboxy1*ic* acid), poly(phthalic acid), poly(mono-2-acryloxyethyl ester), terephthalic polyacid phthalic polyanhydride, polyethylene glycol diacrylate, polyethylene glycol methacrylate, polyethylene glycol dimethacrylate, polyisopropyl acrylate, polysorbitol pentaacrylate, polyvinyl bromoacetate, polychloroprene, poly(di-n-hexyl silylene), poly(di-n-propyl siloxane), polydimethyl silylene, polydiphenyl siloxane, polyvinyl propionate, polyvinyl triacetoxysilane, polyvinyl tris-tert-butoxysilane, polyvinyl butyral, polyvinyl alcohol, polyvinyl acetate, polyethylene co-vinyl acetate, poly(bisphenol-A polysulfone), poly(1,3-dioxepane), poly(1,3-dioxolane), poly(1,4-phenylene vinylene) poly(2,6-dimethyl-1A-phenylene oxide), poly(4-hydroxybenzoic acid), poly(4-methyl pentene-1), poly(4-vinylpyridine), polymethylacrylonitrile, polymethylphenylsiloxane, polymethylsilmethylene, polymethylsilsesquioxane, poly(phenylsilsesquioxane), poly(pyromellitimide-1,4-diphenyl ether), polytetrahydrofuran, polythiophene, poly(trimethylene oxide), polyacrylonitrile, polyether sulfone, polyethylene-co-vinyl acetate, poly(perfluoroethylene propylene), poly(perfluoroalkoxyl alkane), or poly(styrene-acrylonitrile).

By "crosslinking agent" is meant a compound carrying at least two reactive functional groups capable of crosslinking a monomer or a polymer or a mixture of monomers or polymers, during its polymerization.

The crosslinking agent may be chosen from molecules bearing at least two functional groups selected from the group consisting of acrylate, methacrylate, vinyl ether, N-vinyl ether, mercaptoester, thiolene, siloxane, epoxy, oxetane, urethane, isocyanate and peroxide functions.

As crosslinking agent, may be mentioned in particular:
diacrylates, such as 1,6-hexanediol diacrylate, 1,6-hexanediol dimethacrylate, polyethylene glycol dimethacrylate, 1,9-nonanediol dimethacrylate, 1,4-butanediol dimethacrylate, 2,2-bis(4)methacryloxyphenyl) propane, 1,3-butanediol dimethacrylate, 1,10-decanediol dimethacrylate, bis(2-methacryloxyethyl) N,N'-1, 9-nonylene biscarbamate, 1,4-butanediol diacrylate, ethylene glycol diacrylate, 1,5-pentanediol dimethacrylate, 1,4-phenylene diacrylate, allyl methacrylate, N,N'-methylenebisacrylamide, 2,2-bis[4-(2-hydroxy-3-methacryloxypropoxy) phenyl] propane, tetraethylene glycol diacrylate, ethylene glycol dimethacrylate, diethylene glycol diacrylate, triethylene glycol diacrylate, triethylene glycol dimethacrylate, polyethylene glycol diglycidyl ether, N,N-diallylacrylamide, 2,2-bis [4-(2-acryloxyethoxy) phenyl] propane, glycidyl methacrylate;

multifunctional acrylates such as dipentaerythritol pentaacrylate, 1,1,1-trimethylolpropane triacrylate, 1,1,1-trimethylolpropane trimethacrylate, ethylenediamine tetramethacrylate, pentaerythritol triacrylate, pentaerythritol tetraacrylate;

acrylates which also have another reactive function, such as propargyl methacrylate, 2-cyanoethyl acrylate, tricyclodecane dimethanol diacrylate, hydroxypropyl methacrylate, N-acryloxysuccinimide, N-(2-hydroxypropyl) methacrylamide, N-(3-aminopropyl) methacrylamide hydrochloride, N-(t-BOC-aminopropyl) methacrylamide, 2-aminoethyl methacrylate hydrochloride, monoacryloxyethyl phosphate, o-nitrobenzyl methacrylate, acrylic anhydride, 2-(tert-butylamino) ethyl methacrylate, N,N-diallylacrylamide, glycidyl methacrylate, 2-hydroxyethyl acrylate, 4-(2-acryloxyaheoxy)-2-hydroxybenzophenone, N-(phthalimidomethyl) acrylamide, cinnamyl methacrylate.

The catalyst may be chosen from organic, metal, organometallic or inorganometallic catalysts.

As a catalyst, may be mentioned organometallic or inorganometallic complexes of platinum, palladium, titanium, molybdenum, copper, zinc.

According to one embodiment, the composition C2 may further comprise an additional monomer or polymer capable of improving the properties of the microcapsule envelope and/or of giving new properties to the microcapsule envelope.

Among these additional monomers or polymers, may be mentioned monomers or polymers bearing a group sensitive to pH, temperature, UV or IR.

These additional monomers or polymers can induce the rupture of the solid microcapsules and subsequently the release of their contents after stimulation via pH, temperature, UV or IR.

These additional monomers or polymers may be chosen from monomers or polymers bearing at least one reactive functional group chosen from the group consisting of acrylate, methacrylate, vinyl ether, N-vinyl ether, mercaptoester, thiolene, siloxane, epoxy, oxetane and urethane functions, isocyanate and peroxide, and also bearing one of the following groups:
- a hydrophobic group such as a fluorinated group, for example trifluoroethyl methacrylate, trifluoroethyl acrylate, tetrafluoropropyl methacrylate, pentafluoropropyl acrylate, hexafluorobutyl acrylate, or fluorophenyl isocyanate;
- a group sensitive to pH such as primary, secondary or tertiary amines, carboxylic acids, phosphate, sulfate, nitrate or carbonate groups;
- a UV-sensitive or UV-cleavable group (or photochromic group) such as azobenzene, spiropyran, 2-diazo-1,2-naphthoquinone, o-nitrobenzyl, thiol, or 6-nitro-veratroyloxycarbonyl, for example polyethylene oxide)-block-poly(2-nitrobenzylmethacrylate), and other block copolymers, as described in particular in Liu et al., Polymer Chemistry 2013, 4, 3431-3443;
- an IR-sensitive or IR-cleavable group such as o-nitrobenzyl or 2-diazo-1,2-naphthoquinone, for example the polymers described in Liu et al., Polymer Chemistry 2013, 4, 3431-3443; and
- a temperature-sensitive group such as poly(N-isopropylacrylamide).

Step a2)

During step a2), the emulsion (E1) obtained in step a') is added to a composition C3, this step being carried out with stirring, which means that the composition C3 is agitated, typically mechanically, while the emulsion (E1) is added, in order to emulsify the mixture of compositions C1, C2 and C3.

The addition of the emulsion (E1) in the composition C3 is typically carried out dropwise.

During step a2), the emulsion (E1) is at a temperature between 15° C. and 30° C. During step a2), the composition C3 is at a temperature between 15° C. and 30° C.

Under the conditions of addition of step a2), the compositions C2 and C3 are not miscible with each other, which means that the amount (by weight) of the composition C2 capable of being solubilized in the composition C3 is less than or equal to 5%, preferably less than 1%, and preferably less than 0.5%, relative to the total weight of composition C3, and that the amount (by weight) of the composition C3 capable of being solubilized in composition C2 is less than or equal to 5%, preferably less than 1%, and preferably less than 0.5%, relative to the total weight of composition C2.

Thus, when the emulsion (E1) comes into contact with the composition C3 with stirring, the latter is dispersed in the form of drops, called double drops, the dispersion of these emulsion drops (E1) in the continuous phase C3 being called emulsion (E2').

Typically, a double drop formed during step a2) corresponds to a single drop of composition C1 as described above, surrounded by a composition C2 envelope which completely encapsulates the single drop.

The double drop formed during step a2) may also comprise at least two single drops of composition C1, the single drops being surrounded by a composition C2 envelope which completely encapsulates the single drops.

Thus, the double drops comprise a core consisting of one or more single drops of composition C1, and a layer of composition C2 surrounding the core.

The resulting emulsion (E'2) is generally a double polydisperse emulsion (C1-in-C2-in-C3 emulsion or C1/C2/C3 emulsion), which means that the double drops do not have a clear size distribution in the emulsion (E2').

The immiscibility between the compositions C2 and C3 makes it possible to avoid mixing between the layer of composition C2 and the composition C3 and thus ensures the stability of the emulsion (E'2).

The immiscibility between the compositions C2 and C3 also makes it possible to prevent the active ingredient of the composition C1 from migrating from the core drops to the composition C3.

To carry out step a2), it is possible to use any type of stirrer usually used to form emulsions, such as for example an ultrasonic homogenizer, a membrane homogenizer, a high-pressure homogenizer, a colloid mill, a high shear disperser or a high speed homogenizer.

Composition C3

According to the invention, the viscosity of the composition C3 at 25° C. is greater than 10 000 mP·s at a shear rate of 10 s$^{-1}$ and less than 10 000 mP·s at the shearing speed at which c') is performed, i.e. at a shear rate of between 100 s$^{-1}$ and 100,000 s$^{-1}$.

The composition C3 may also be referred to as a gelled composition.

Preferably, the viscosity of the composition C3 at 25° C. is between 15,000 mP·s and 100,000 mP·s at a shear rate of 10 s$^{-1}$ and less than 5,000 mP·s at the shear rate at which c') is performed, i.e. at a shear rate of between 100 s$^{-1}$ and 100,000 s$^{-1}$.

Preferably, the interfacial tension between compositions C2 and C3 is low. The low interfacial tension between the compositions C2 and C3 also advantageously makes it possible to ensure the stability of the emulsion (E2) or (E'2).

According to one embodiment, the ratio between the emulsion (E1) volume and the composition C3 volume varies between 1:10 and 10:1. Preferably, this ratio is between 1:9 and 3:1, preferably between 1:9 and 1:1.

This ratio may be adapted to control the total amount of encapsulated active ingredient among the resulting population of polymerized microcapsules.

According to one embodiment, the composition C3 comprises at least one branched polymer, preferably with a molecular weight greater than 5,000 g·mol$^{-1}$, preferably between 10,000 g·mol$^{-1}$ and 500,000 g·mol$^{-1}$, for example between 50,000 g·mol$^{-1}$ and 300,000 g·mol$^{-1}$.

By "branched polymer" is meant a polymer having at least one branch point between its two end groups, a branch point being a point of a chain on which is fixed a side chain also called a branch or hanging chain.

Among branched polymers, may be mentioned, for example, graft or comb polymers or star polymers or dendrimers.

According to one embodiment, the composition C3 comprises at least one polymer with a molecular weight greater than 5,000 g/mol.

As a polymer that may be used in the composition C3, mention may be made of the following compounds, used alone or mixed together:
- cellulose derivatives, such as cellulose ethers: methyl cellulose, ethyl cellulose, hydroxyethyl cellulose, methylhydroxyethyl cellulose, ethylhydroxyethyl cellulose, carboxymethyl cellulose, hydroxypropyl cellulose or methylhydroxypropyl cellulose;

polyacrylates (also called carbomers), such as polyacrylic acid (PAA), polymethacrylic acid (PMAA), poly(hydroxyethyl methacrylate) (pHEMA), poly(N-2-hydroxypropyl methacrylate) (pHPMA);

polyacrylamides such as poly(N-isopropylacrylamide) (PNIPAM);

polyvinylpyrrolidone (PVP) and its derivatives;

polyvinyl alcohol (PVA) and its derivatives;

poly(ethylene glycol), poly(propylene glycol) and their derivatives, such as poly(ethylene glycol) acrylate/methacrylate, poly(ethylene glycol) diacrylate/dimethacrylate, polypropylene carbonate;

polysaccharides such as carrageenans, carob gum or tara gums, dextran, xanthan gums, chitosan, agarose, hyaluronic acids, gellan gum, guar gum, arabic gum, tragacanth gum, diutane gum, oat gum, karaya gum, ghatti gum, curdlan gum, pectin, konjac gum;

protein derivatives such as gelatin, collagen, fibrin, polylysine, albumin, casein;

silicone derivatives such as polydimethylsiloxane (also called dimethicone), alkyl silicones, aryl silicones, alkyl aryl silicones, polyethylene glycol dimethicones, polypropylene glycol dimethicone;

waxes, such as diester waxes (alkanediol diesters, hydroxyl acid diesters), triester waxes (triacylglycerols, triesters of alkane-1,2-diol, w-hydroxy acid and fatty acid, esters of hydroxymalonic acid, fatty acid and alcohol, triesters of hydroxyl acids, fatty acid and fatty alcohol, triesters of fatty acid, hydroxyl acid and diol) and polyester waxes (polyesters of fatty acids). The fatty acid esters which may be used as waxes in the context of the invention are, for example, cetyl palmitate, cetyl octanoate, cetyl laurate, cetyl lactate, cetyl isononanoate and stearate. cetyl, stearyl stearate, myristyl stearate, cetyl myristate, isocetyl stearate, glyceryl trimyristate, glyceryl tripalmitate, glyceryl monostearate, or cetyl glyceryl palmitate;

fatty acids that may be used as waxes such as cerotic acid, palmitic acid, stearic acid, dihydroxystearic acid, behenic acid, lignoceric acid, arachidic acid, myristic acid, lauric acid, tridecyclic acid, pentadecyclic acid, margaric acid, nonadecyclic acid, henicosylic acid, tricosylic acid, pentacosylic acid, heptacosylic acid, montanic acid or nonacosylic acid;

fatty acid salts, in particular fatty acid aluminum salts, such as aluminum stearate, hydroxyl aluminum bis(2-ethylhexanoate);

isomeric jojoba oil;

hydrogenated sunflower oil;

hydrogenated coconut oil;

hydrogenated lanolin oil;

castor oil and its derivatives, especially modified hydrogenated castor oil or compounds obtained by esterification of castor oil with fatty alcohols;

polyurethanes and their derivatives;

styrenic polymers such as styrene butadiene; and polyolefins such as polyisobutene.

According to one embodiment, the composition C3 comprises solid particles such as clays, silicas and silicates.

As solid particles that may be used in the composition C3, mention may be made of clays and silicates belonging, in particular, to the category of phyllosilicates (also known as layered silicas). By way of example of a silicate that may be used in the context of the invention, mention may be made of bentonite, hectorite, attapulgite, sepiolite, montmorillonite, saponite, sauconite, nontronite, kaolinite, talc., sepiolite, chalk. Fumed synthetic silicas may also be used. The clays, silicates and silicas mentioned above may advantageously be modified by organic molecules such as polyethers, ethoxylated amides, quaternary ammonium salts, long-chain diamines, long-chain esters, polyethylene glycols, polypropylene glycols.

These particles may be used alone or mixed together.

According to one embodiment, the composition C3 comprises at least one polymer with a molecular weight greater than 5,000 g/mol and solid particles. Any mixture of the compounds mentioned above may be used.

Step b)

In step b), the emulsion (E2) or the emulsion (E'2), consisting of polydispersed drops dispersed in a continuous phase, is subjected to shear, for example in a mixer, at a shear rate. between 100 $s^{-1}$ and 100,000 $s^{-1}$.

According to one embodiment, the shear rate applied in step b) is between 100 $s^{-1}$ and 50,000 $s^{-1}$.

Preferably, the shear rate applied in step b) is between 1000 $s^{-1}$ and 20,000 $s^{-1}$.

During step b), the emulsion (E2) or (E'2) is introduced into a mixer and is then subjected to shearing which results in the formation of a third emulsion, emulsion (E3) or (E'3), respectively.

Since the viscosity of the composition C3 is less than 10 000 mP·s at the shear rate at which step b) is carried out, the emulsion (E2) or (E'2) may easily be mixed using any type of emulsion agitator. Thus, in order to carry out step b), any type of stirrer usually used to form emulsions, such as, for example, a mechanical stirrer, a static emulsifier, an ultrasonic homogenizer, a membrane homogenizer, a high pressure homogenizer, a colloid mill, a high shear disperser or a high speed homogenizer.

The emulsion (E3) or (E'3) is chemically identical to the emulsion (E2) (or (E'2)) respectively) but it consists of monodisperse drops, and non-polydisperse as (E2) or (E'2).

Typically, the emulsion (E'3) consists of a dispersion of double drops comprising a core consisting of one or more single drops of composition C1, and a layer of composition C2 surrounding the core, the double drops being dispersed in the composition C3.

The difference between the emulsion (E2) (or (E'2)) and the emulsion (E3) (or (E'3)) is the droplet size variation: the drops of the emulsion (E2) (or (E'2)) are polydisperse in size while the drops of the emulsion (E3) (or (E'3)) are monodisperse due to the fragmentation mechanism occurring during step c).

The drops of emulsion (E2) (or (E'2)) can not be effectively fragmented into fine and monodisperse emulsion drops (E3) (or (E'3)) if only a high shear stress is applied.

The shear stress a applied to a drop of emulsion (E2) (or (E'2)) is defined as the tangential force per unit area of drop resulting from the macroscopic shear applied to the emulsion during its agitation during step c).

The shear stress $\sigma$ (expressed in Pa), the viscosity of the composition C3 $\eta$ (expressed in Pa·s) and the shear rate $\gamma$ (expressed in $s^{-1}$) applied to the emulsion (E2) (or (E'2)) during its stirring during step c) are connected by the following equation:

$$\sigma = \eta \gamma$$

Thus, the combination of the viscosity of the composition C3 and the shear applied by the mixer makes it possible to apply a high shear stress to the emulsion drops (E2) (or (E'2)) and thus to break them into monodisperse drops.

Step c)

Step c) consists of subjecting the emulsion (E3) (or (E'3)) to polymerization, which will allow polymerization of the composition C2.

According to one embodiment of the invention, during step c), the single emulsion drops (E3) consisting of crosslinkable composition C2, are crosslinked and thus converted into viscoelastic polymeric microparticles.

According to another embodiment, during step c), the envelope of the emulsion (E'3) double drops, composed of crosslinkable composition C2, is crosslinked, and thus converted into a viscoelastic polymeric envelope, encapsulating and protecting the active ingredient against its release in the absence of a mechanical stress.

During step c), the emulsion (E3) (or (E'3)) is allowed to stand for a period of up to 100 hours. During this time, many emulsion destabilization phenomena well known to those skilled in the art may make the emulsion (E3) (or (E'3)) again polydisperse, such as coalescence, ripening, sedimentation or creaming. An important feature of the present invention is to suppress these phenomena throughout the duration of step c). In fact, since the viscosity of the composition C3 is greater than 10 000 mP·s at a shear rate of 10 $s^{-1}$, the mobility of the emulsion drops (E3) or (E'3) is very greatly reduced and the destabilization kinetics of the emulsion is very slow compared to the duration of step c).

Thus, the very high viscosity of the composition C3 at a shear rate of 10 $s^{-1}$ ensures the stability of the emulsion (E3) or (E'3) until step c) is completed.

According to the invention, the term "polymerization" encompasses any polymerization that does not need to be initiated by exposure to a light source. In particular, the polymerization according to the invention is not photoinitiated.

The polymerization according to the invention may, for example, be initiated by exposure to heat (thermal initiation), or simply by bringing the reagents into contact with each other, or by simply bringing the reagents into contact with a catalyst.

According to one embodiment, the method of the invention does not include a step of exposure to a UV light source.

According to one embodiment, the polymerization step c) is not a photopolymerization step.

According to one embodiment, the polymerization step c) of the composition C2 is carried out for a period of between 8 hours and 100 hours.

According to one embodiment, the polymerization step c) of the composition C2 is carried out at a temperature of between 20° C. and 80° C.

Preferably, the polymerization step c) of the composition C2 is carried out for a period of between 8 hours and 100 hours, at a temperature between 20° C. and 80° C.

The composition obtained at the end of step c), comprising microparticles or solid microcapsules dispersed in the composition C3, is ready for use and may be used without being washed or without further treatment.

The thickness of the envelope of the microcapsules thus obtained is typically between 10 nm and 2.5 µm, preferably between 100 nm and 1000 nm.

According to one embodiment, the microparticles or the solid microcapsules obtained at the end of step c) are free of water and/or surfactant.

The method of the invention has the advantage of not requiring water in any of the steps described. The method of the invention thus makes it possible to encapsulate compounds that are sensitive to water.

The method of the invention has the advantage of not requiring a surfactant, in any of the steps described. The method of the invention thus makes it possible to reduce the presence of additives which could modify the properties of the final product obtained after release of the active ingredient.

EXAMPLES

Example 1

Preparation of Solid Microparticles

This example demonstrates: (i) the use of a gelled composition C3 making it possible to manufacture drops smaller than 20 µm and then to prevent the destabilization of the emulsion for 48 hours; (ii) obtaining crosslinked microparticles after 48 hours.

Composition of C'2 and C3:
  The composition C'2 is a polymerizable PDMS preparation prepared with the two-component Sylgard 184 kit manufactured by Dow Corning. Component #1 of the kit includes the following products (data provided by Dow Corning):
    between 55.0% and 75.0% of dimethyl, methylhydrogen siloxane,
    between 15.0% and 35.0% of dimethyl siloxane, dimethylvinyl-terminated,
    between 10.0% and 30.0% of dimethylvinylated and trimethylated silica,
    between 1.0% and 5.0% of tetramethyl tetravinyl cyclotetrasiloxane, less than 0.10% ethylbenzene.
  Component #2 of the kit includes the following products (data provided by Dow Corning):
    less than 200 ppm of a platinum complex,
    between 55.0 and 75.0% dimethyl siloxane, dimethylvinyl terminated,
    between 30.0 and 50.0% dimethylvinylated and trimethylated silica,
    less than 1.0% tetra (trimethylsiloxy) silane,
    0.5% xylene, o 0.2% ethylbenzene.
  This kit may be considered as the mixture of several polymers, of several crosslinking agents, and of a catalyst within the meaning of the invention.
  Composition C'2 comprises 15% of component No. 1 and 85% of component No. 2.
  Composition C3 is a solution of carbomer Tego 340FD (Evonik, Essen, Germany) at 4% by weight in distilled water. The solution is agitated to 2000 rpm for 20 minutes using a propeller stirrer. The pH is then adjusted to 6 with 2M sodium hydroxide solution. The viscosity of the C3 composition at 10 $s^{-1}$ is 52,000 mP·s.

Manufacture of Microparticles:
  Step a"): The composition C'2 is added dropwise to the composition C3 with stirring at 500 rpm until a ratio C'2: C3=10:90 by weight. The stirrer used fort this step is a mechanical stirrer (Heidolph RZR 2021) equipped with a deflocculating propeller of diameter 3 cm.
  Step b): The emulsion (E2) obtained in the preceding step is introduced into a Couette type mixer manufactured by TSR33. This mixer consists of two concentric cylinders, one mobile and the other fixed, separated by a gap of 100 µm. The rotation of the movable cylinder makes it possible to apply a uniform shear to all the emulsion contained in the gap. The emulsion (E2) is subjected to a shear of 1000 $s^{-1}$. At this shear rate, the viscosity of C3 is only 2,500 mP·s, which allows the emulsion (E2) to pass easily inside the mixer.

Step c): The emulsion E3) thus obtained is left for 48 hours at rest to allow the polymerization of the particles.

Figure 2:
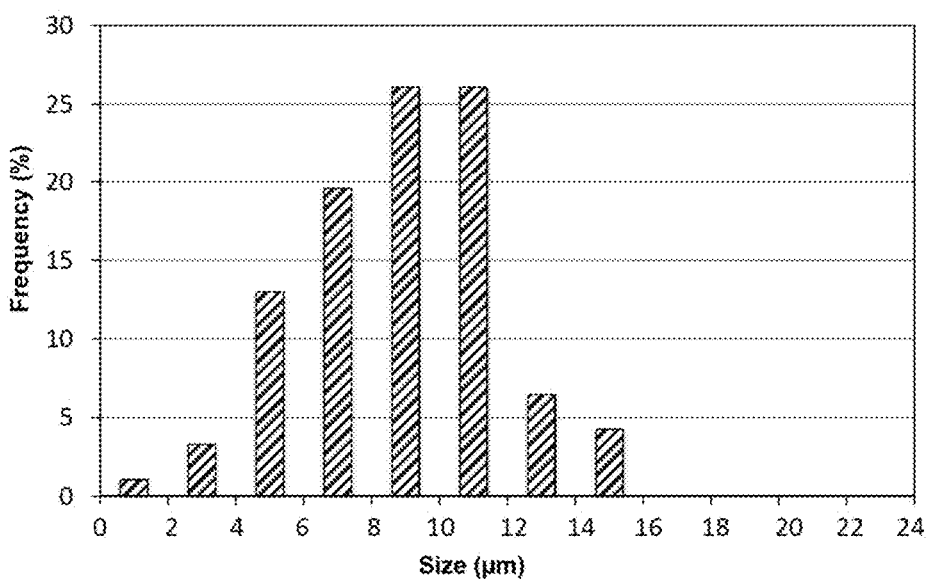
FIG. 2 shows the size distributions of the capsules obtained at different stages of an embodiment of the method of the present disclosure.

The particles are imaged by interference contrast optical microscopy before and after step c). An image analysis carried out with Image J software makes it possible to obtain the size distribution. FIGS. 1 and 2 show the size distributions of the capsules obtained at different stages of the method of the invention.

Before step c), the emulsion drops (E3) have an average size of 8 μm and the width of the size distribution has a width at half height (considered as a simple way to evaluate the monodispersity) of 5 μm (FIG. 1). After step c), the polymerized particles have an average size of 8 μm and the width of the size distribution has a width at half height of 5 μm (FIG. 2).

The size distribution is therefore the same before and after the 48 hours of polymerization: the emulsion (E3) has not undergone any destabilization thanks to the high viscosity of the composition C3.

Example 2

Preparation of Solid Microcapsules

This example demonstrates: (i) the use of a gelled composition C3 in order to let the double drops obtained at the end of the shearing step rest for 48 hours without any destabilization; (ii) obtaining crosslinked capsules after 48 hours.

Composition of C1, C2 and C3:

Composition C1 is a mixture of paraffin oils (Sigma, St. Louis, Miss.) with Aerosil 816 (Essen, Germany) (active ingredient) at 4% by weight.

Composition C2 is a polymerizable PDMS preparation prepared with the Dow Corning Sylgard 184 Two-Component Kit. Composition C2 comprises 30% of component No. 1 and 70% of component No. 2.

Composition C3 is a solution of carbomer Tego 340FD (Evonik, Essen, Germany) at 4% by weight in distilled water. The solution is stirred at 2000 rpm for 20 minutes using a propeller stirrer. The pH is then adjusted to 6 with 2M sodium hydroxide solution. The viscosity of the composition C3 at 10 $s^{-1}$ is 52,000 mP·s.

Manufacture of Microcapsules:

A mechanical stirrer (Heidolph RZR 2021) equipped with a 3 cm diameter deflocculating stirring propeller is used to carry out all the emulsification steps.

Step a1): the composition C1 is added dropwise to the composition C2 with stirring at 200 rpm until a ratio C1:C2=20:80 by weight. Stirring is then maintained at 200 rpm for 30 minutes.

Step a2): the emulsion (E1) thus obtained is added dropwise to the composition C3 with stirring at 500 rpm until a ratio E1:C3=10:90 by weight.

Step b): The emulsion (E2) thus obtained is stirred at 500 rpm for 20 minutes. Under these conditions, the shear applied to the emulsion (E2), although very little controlled, may be estimated at less than 500 $s^{-1}$ (for the details of the calculation, refer to: Metzner A B, Otto R E. of non-Newtonian fluids AICHE J (1957) 3:3-10, Wu, J et al., Estimate of agitator flow shear rate, AIChE J (2006) 52:2323-2332).

Step c): the emulsion (E3) thus obtained is left for 48 hours at rest without stirring to allow polymerization of the capsules.

Figure 3:
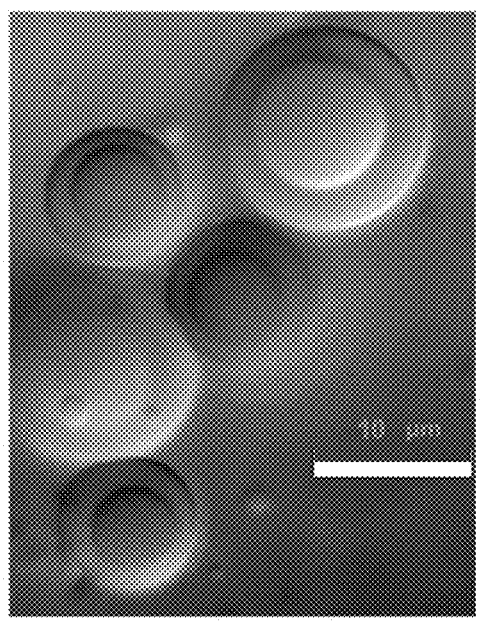
FIG. 3 shows an embodiment of double emulsion drops (E3).
Figure 4:
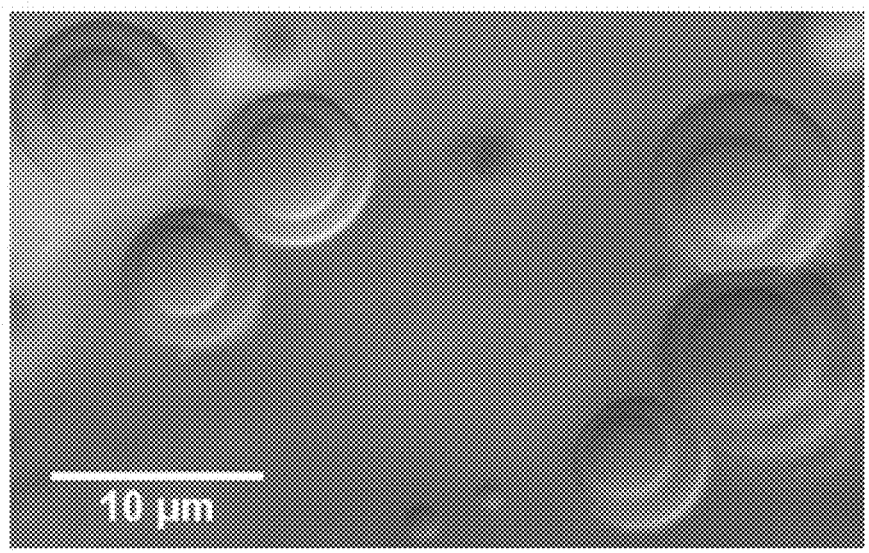
FIG. 4 shows an embodiment of polymerized capsules.
Figure 5:
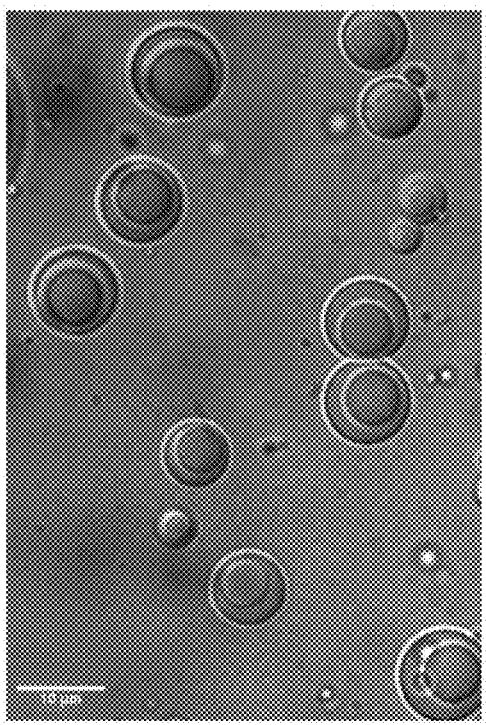
FIG. 5 shows an embodiment of polymerized capsules imaged after being mechanically sheared between a slide and a microscope slide, rubbed against each.

FIGS. 3 to 5 show interference contrast microscopy photographs taken at different stages of manufacture.

FIG. 3 shows double emulsion drops (E3) after step b).

FIG. 4 shows polymerized capsules after step c).

FIG. 5 shows polymerized capsules imaged after being mechanically sheared between a slide and a microscope slide, rubbed against each other. The capsules are intact after this step, which shows that they are effectively polymerized.

An image analysis carried out with Image J software makes it possible to obtain the size distribution of the capsules at the different stages of manufacture. After step b), the double drops have an average size of 6.0 μm and the width of the size distribution has a width at half height (considered as a simple way to evaluate the monodispersity) of 5.5 μm. After step c), the polymerized capsules have an average size of 5.8 μm and the width of the size distribution has a width at mid-height of 5.0 μm. The size distribution is therefore the same before and after the 48 hours of polymerization: the emulsion (E3) has not undergone any destabilization thanks to the high viscosity of the composition C3.

Example 3

Preparation of Solid Microparticles According to the Invention

This example demonstrates: (i) the use of a gel composition C3 within the meaning of the invention making it possible to manufacture drops smaller than 20 μm and then to prevent the destabilization of the emulsion for 48 hours; (ii) obtaining crosslinked microparticles after 48 hours.

Composition of C'2 and C3:

The C'2 composition is a polymerizable PDMS preparation prepared with the Dow Corning Sylgard 184 Two-Component Kit. Composition C'2 comprises 15% of component No. 1 and 85% of component No. 2.

Composition C3 is a solution of alginate at 10% by weight. The viscosity of the C3 composition is 16,980 mP·s at 10 $s^{-1}$ and 6,670 mP·s at 100 $s^{-1}$. This composition C3 is gelled in the sense of the invention.

Manufacture of Microparticles:

Step a"): The composition C'2 is added dropwise to the composition C3 with stirring at 500 rpm until a ratio C'2:C3=10:90 by weight. The stirrer used for this step is a mechanical stirrer (Heidolph RZR 2021) equipped with a deflocculating propeller of diameter 3 cm.

Step b): The emulsion (E2) obtained in the preceding step is stirred at 500 rpm for 10 minutes.

Step c): The emulsion E3) thus obtained is left for 48 hours at rest to allow the polymerization of the particles.

The particles are imaged by interference contrast optical microscopy before and after step c). An image analysis carried out with Image J software makes it possible to obtain the size distribution.

Before step c), the emulsion drops (E3) have an average size of 6.5 μm and the width of the size distribution has a width at half height of 3 μm. After step c), the polymerized particles have an average size of 7 μm and the width of the size distribution has a width at half height of 3 μm.

The size distribution is therefore the same before and after the 48 hours of polymerization: the emulsion (E3) has not undergone any destabilization thanks to the high viscosity of the composition C3.

Example 4 (Comparative)

Preparation of Solid Microparticles

This example demonstrates the use of an ungelled composition C3 within the meaning of the invention that does not make it possible to prevent the destabilization of the emulsion for 48 hours.

Composition of C'2 and C3:

The C'2 composition is a polymerizable PDMS preparation prepared with the Dow Corning Sylgard 184 Two-Component Kit. Composition C'2 comprises 15% of component No. 1 and 85% of component No. 2.

The composition C3 is a solution of alginate 5% by weight. The viscosity of composition C3 is 1340 mP·s at 10 $S^{-1}$ and 890 mP·s at 100 $s^{-1}$. This composition C3 is not gelled in the sense of the invention.

Manufacture of Microparticles:

Step a"): The composition C'2 is added dropwise to the composition C3 with stirring at 500 rpm until a ratio C'2:C3=10:90 by weight. The stirrer used for this step is a mechanical stirrer (Heidolph RZR 2021) equipped with a deflocculating propeller of diameter 3 cm.

Step b): The emulsion (E2) obtained in the preceding step is stirred at 500 rpm for 10 minutes.

Step c): The emulsion E3) thus obtained is left for 48 hours at rest to allow the polymerization of the particles.

The particles are imaged by interference contrast optical microscopy before and after step c). An image analysis carried out with Image J software makes it possible to obtain the size distribution. Before step c), the emulsion drops (E3) have an average size of 15 μm and the width of the size distribution has a width at half height of 11 μm. After step c), the polymerized particles have an average size of 31 μm and the width of the size distribution has a width at midheight of 12 μm.

The emulsion (E3) has therefore undergone a major destabilization due to the unsatisfactory properties of C3.

What is claimed is:

1. A method for preparing solid microcapsules comprising the steps of:
    a) adding, with stirring, a composition C'2 in a composition C3, the compositions C'2 and C3 not being miscible with each other, the composition C'2 being either a cross-linkable monophasic composition C2 or an emulsion (E1) comprising drops of a composition C1, comprising at least one active ingredient, dispersed in a cross: linkable polymeric composition C2,
    the compositions C1 and C2 not being miscible in each other,
    the viscosity of composition C3 being greater than 10,000 mPa·s at 25° C. at a shear rate of 10 $s^{-1}$ and being less than 10,000 mPa·s at 25° C. at a shear rate of between 100 $s^{-1}$ and 100,000 $s^{-1}$,
    wherein an emulsion (E2) comprising drops of composition C'2 dispersed in composition C3, is obtained;
    b) applying a shear to the emulsion (E2), the applied shear rate being between 100 $s^{-1}$ and 100,000 $s^{-1}$,
    wherein an emulsion (E3) is obtained comprising controlled-size drops of composition C'2 dispersed in the composition C3; and
    c) polymerizing of the composition C'2, wherein solid microcapsules dispersed in the composition C3 are obtained.

2. The method according to claim 1, wherein the composition C'2 is an emulsion (E1) obtained by adding, with stirring, a composition C1 comprising at least one active ingredient, in a polymeric composition C2, the compositions C1 and C2 being immiscible in one another.

3. The method according to claim 2, comprising the steps of:
    a1) adding, with stirring, a composition C1, comprising at least one active ingredient, in a polymeric composition C2, the compositions C1 and C2 not being miscible with each other,
    wherein an emulsion (E1) comprising drops of composition C1 dispersed in composition C2 is obtained;
    a2) adding, with stirring, the emulsion (E1) in a composition C3, the compositions C2 and C3 not being miscible with each other,
    the viscosity of composition C3 being greater than 10,000 mPa·s at 25° C. at a shear rate of 10 $s^{-1}$ and being less than 10,000 mPa·s at 25° C. at a shear rate of between 100 $s^{-1}$ and 100,000 $s^{-1}$,
    wherein a double emulsion (E'2) is obtained comprising drops dispersed in the composition C3;
    b) applying shear to the emulsion (E'2), the applied shear rate being between 100 $s^{-1}$ and 100,000 $s^{-1}$,
    wherein a double emulsion (E'3) is obtained comprising controlled-size drops dispersed in the composition C3; and
    c) polymerizing of the composition C2, wherein solid microcapsules dispersed in the composition C3 are obtained.

4. The method according to claim 1, wherein the composition C2 is a liquid the viscosity of which at 25° C. is between 500 mPa·s and 100,000 mPa·s.

5. The method according to claim 1, wherein the composition C2 comprises at least one monomer or polymer, at least one crosslinking agent, and optionally at least one catalyst.

6. The method according to claim 1, wherein the composition C2 does not include a photoinitator.

7. The method according claim 1, wherein the composition C2 comprises from 0.001% to 70% by weight of crosslinking agent relative to the total weight of the composition.

8. The method according to claim 1, wherein the active ingredient is solubilized in the composition C1 or is dispersed in the form of solid particles in the composition C1.

9. The method according to claim 1, wherein the composition C3 comprises at least one branched polymer, and/or at least one polymer of molecular weight greater than 5,000 g·$mol^{-1}$, and/or solid particles such as silicates.

10. The method according to claim 1, wherein the viscosity of the composition C3 at 25° C. is between 15,000 mPa·s and 100,000 mPa·s at a shear rate of 10 $s^{-1}$ and less than 5,000 mPa·s at a shear rate of between 100 $s^{-1}$ and 100,000 $s^{-1}$.

11. The method according to claim 1, wherein the shear rate applied in step b) is between 10 $s^{-1}$ and 1,000 $s^{-1}$.

12. The method according to claim 1, not including a step of exposure to a UV light source.

13. The method according to claim 1, wherein the polymerization step of the composition C2 is carried out for a period between 8 hours and 100 hours.

14. The method according to claim 1, wherein the step of polymerizing the composition C2 is carried out at a temperature between 20° C. and 80° C.

15. The method according to claim 1, wherein the polymerization step of the composition C2 is carried out for a period of between 8 hours and 100 hours, at a temperature between 20° C. and 80° C.

16. The method according to claim 9, wherein the composition C3 comprises at least one branched polymer with a molecular weight greater than 5,000 g·mol$^{-1}$.

* * * * *